US008771782B2

(12) United States Patent
O'Neill et al.

(10) Patent No.: US 8,771,782 B2
(45) Date of Patent: Jul. 8, 2014

(54) IMPLANTABLE MEDICAL DEVICES

(75) Inventors: Liam O'Neill, Midleton (IE); John O'Donoghue, Dungarvan (IE); Joe O'Keeffe, Fermoy (IE); Peter Dobbyn, Midleton (IE)

(73) Assignee: Enbio Limited, Dublin (IE)

( * ) Notice: Subject to any disclaimer, the term of this patent is extended or adjusted under 35 U.S.C. 154(b) by 0 days.

(21) Appl. No.: 13/315,902

(22) Filed: Dec. 9, 2011

(65) Prior Publication Data
US 2012/0171354 A1 Jul. 5, 2012

Related U.S. Application Data

(60) Provisional application No. 61/422,491, filed on Dec. 13, 2010.

(51) Int. Cl.
B05D 3/00 (2006.01)
C23C 14/30 (2006.01)
B05D 1/04 (2006.01)

(52) U.S. Cl.
USPC ............ 427/2.1; 427/2.24; 427/331; 427/596

(58) Field of Classification Search
USPC ................................ 427/331, 596
See application file for complete search history.

(56) References Cited

U.S. PATENT DOCUMENTS

| 4,929,319 | A | 5/1990 | Dinter et al. |
| 6,387,379 | B1* | 5/2002 | Goldberg et al. ............. 424/400 |
| 7,250,195 | B1* | 7/2007 | Storey et al. .................. 427/475 |
| 7,455,892 | B2 | 11/2008 | Goodwin et al. |
| 7,666,748 | B2* | 2/2010 | Jain ............................... 438/300 |
| 2004/0176749 | A1 | 9/2004 | Lohmann et al. |
| 2005/0142163 | A1* | 6/2005 | Hunter et al. .................. 424/423 |
| 2005/0260331 | A1* | 11/2005 | Wang et al. ..................... 427/2.1 |
| 2007/0029500 | A1* | 2/2007 | Coulombe et al. .......... 250/423 F |
| 2007/0225700 | A1 | 9/2007 | Kuhner |
| 2008/0118734 | A1* | 5/2008 | Goodwin et al. ............. 428/221 |
| 2008/0199513 | A1 | 8/2008 | Beretta et al. |
| 2008/0237484 | A1 | 10/2008 | Morfill et al. |
| 2012/0089084 | A1* | 4/2012 | O'Keeffe et al. ............... 604/24 |

FOREIGN PATENT DOCUMENTS

| EP | 351950 A * | 1/1990 |
| WO | WO 2005/106477 A2 | 11/2005 |
| WO | WO 2005/110626 A2 | 11/2005 |
| WO | WO 2007/106212 A1 | 9/2007 |
| WO | WO 2008/033897 A1 | 3/2008 |

(Continued)

OTHER PUBLICATIONS

Siow et al., "Plasma Methods for the Generation of Chemically Reactive Surfaces for Biomolecule Immobilization and Cell Colonization—A Review", *Plasma Process and Polymers* 2006, vol. 3, pp. 392-418.

(Continued)

*Primary Examiner* — Cachet Sellman
(74) *Attorney, Agent, or Firm* — Bookoff McAndrews, PLLC

(57) ABSTRACT

The present invention is directed to methods for producing a coated substrate, including dissolving at least one biomolecule to form a solution; nebulizing the solution to form a liquid aerosol; combining the liquid aerosol and a plasma to form a coating; and depositing, in the absence of reactive monomers, the coating onto a substrate surface. In an aspect, the substrate can be an implantable medical device.

22 Claims, 2 Drawing Sheets

(56) References Cited

FOREIGN PATENT DOCUMENTS

| WO | WO 2010/022871 A1 | 3/2010 |
|---|---|---|
| WO | WO 2010/105829 A1 | 9/2010 |
| WO | WO 2010/146438 A1 | 12/2010 |

OTHER PUBLICATIONS

Allcock et al., "Plasma Surface Functionaliztion of Poly[bis(2,2,2-trifluoroethoxy)phosphazene] Films and Nanofibers", 2007 American Chemical Society, Published on Web Jun. 23, 2007, *Langmuir* 2007, vol. 8 23, pp. 8103-8107.

Heyse et al., "Dielectric Barrier Discharge at Atmospheric Pressure as a Tool to Deposit Versatile Organic Coatings at Moderate Power Input", *Plasma Process and Polymers* 2007, vol. 4, pp. 145-157.

Roth et al., "Atmospheric Pressure Plasma Sources", Ch. 15 in *Industrial Plasma Engineering*, vol. 2:*Applications to Non-thermal Plasma Processing*, Institute of Physics Publishing, 2001, pp. 37-73.

Okazaki et al., "Appearance of stable glow discharge in air, argon, oxygen and nitrogen at atmospheric pressure using a 50 Hz source", *J. Phys. D; Appl. Phys.* vol. 26 (1993), pp. 889-892.

Ladwig et al., "Atmospheric plasma deposition of glass coatings on aluminum", *Surface & Coatings Technology*, vol. 201 (2006), pp. 6460-6464.

O'Neill & O'Sullivan, "Polymeric Coatings Deposited From an Aerosol-Assisted Non-thermal Plasma Jet", *Chemical Vapor Deposition* 2009, vol. 15, pp. 1-6.

Hunt et al., "The design and production of Co-Cr alloy implants with controlled surface topography by CAD-CAM method and their effects on osseointegration", *Biomaterials* vol. 26 (2005), pp. 5890-5897.

Heyse et al., "Protein Immobilization Using Atmospheric-Pressure Dielectric-Barrier Discharges: A Route to a Straightforward Manufacture of Bioactive Films", *Plasma Processes and Polymers* 2008, vol. 5, pp. 186-191.

Heyse et al., "Exploration of Atmospheric Pressure Plasma Nanofilm Technology for Straightforward Bio-Actice Coating Deposition: Enzymes, Plasmas and Polymers, an Elegant Synergy", *Plasma Processes and Polymers* 2011, vol. 8, pp. 965-974.

O'Hare et al., "Anti-microbial coatings by agent entrapment in coatings deposited via atmospheric pressure plasma liquid deposition", *Surface and Interface Analysis* 2006; vol. 38, pp. 1519-1524.

Ortore et al., "Grazing-incidence small-angle X-ray scattering from alkaline phosphatase immobilized in atmospheric plasmapolymer coatings", *Applied Surface Science* vol. 254 (2008), pp. 5557-5563.

* cited by examiner

IMPLANTABLE MEDICAL DEVICES

RELATED APPLICATIONS

The present application claims priority to U.S. Provisional Patent Application No. 61/422,491, filed on Dec. 13, 2010, the disclosure of which is hereby incorporated by reference.

FIELD OF THE INVENTION

The present invention relates to a method of depositing a biomolecule onto a substrate using plasma, such as a non-thermal atmospheric pressure discharge.

BACKGROUND OF THE INVENTION

In general there are two plasma types, namely thermal equilibrium and non-isothermal equilibrium plasmas. Thermal equilibrium plasmas are typically hot with temperatures ~10,000 K and are used in industry as plasma torches, jets and arcs for welding. These hot plasma systems are also used in thermal spray coating where they can be used to deposit metallic and ceramic coatings onto metal surfaces for applications as diverse as producing biocompatible hydroxyapatite coatings on medical implants to the deposition of protective coatings on gas turbine components. Despite the widespread use of thermal plasmas to produce biocompatible hydroxyapatite ceramic coatings, their applications are limited by the high thermal energy within these devices which prevent these devices from depositing temperature sensitive materials such as proteins, polysaccharides and other biomaterials.

In contrast, non-isothermal plasmas are generally cool and can be employed in manufacturing processes including surface cleaning (removal of unwanted contaminants), etching (removal of bulk substrate material), activation (changing surface energies) and deposition of functional thin film coatings onto surfaces. Historically, these coating devices were limited to vacuum conditions and used only gas phase precursors to produce coatings. However, plasma systems have been widely used to modify surfaces to allow for subsequent attachment of biomolecules through traditional wet chemistry techniques, and this area has been extensively reviewed by Siow et al (Plasma Processes and Polymers, 2006, 3, pages 392-418).

Recent years have seen the development of plasma devices that operate at atmospheric pressure and which can also produce functional coatings using gas phase monomers, and a typical example is seen in Allcock et al, Langmuir, 2007, 23, 8103-8107. However, the switch from vacuum systems to ambient pressure also allows for the use of precursors other than gas phase monomers in the production of thin films. U.S. Pat. No. 4,929,319 discloses a process for treating a plastic substrate in which a liquid aerosol is introduced into an atmospheric corona discharge while a flat plastic substrate is passed through the corona discharge.

U.S. Pat. No. 7,455,892 discloses a method for producing a coating wherein a polymer forming material is atomized into a homogeneous atmospheric pressure plasma glow discharge in order to produce a polymeric coating on a substrate. The list of potential monomers disclosed includes numerous materials which are well known to polymerize under exposure to free radicals or UV radiation to produce a coating. These precursors typically contain vinyl, cyclic or other reactive groups.

WO 2007/106212 discloses a plasma system which combines an atmospheric pressure plasma activation coupled to a vacuum deposition chamber in order to deposit a biomolecule on a surface. The idea of combing vacuum chambers and atmospheric pressure plasma jets into one system represents a complex engineering challenge.

In traditional plasma polymerization systems, it is standard practice to use monomers that contain reactive groups that undergo free radical or ionic polymerization reactions and the presence of these groups allow the monomers to produce a dry, polymerized coatings without the use of high energy plasmas. It has been possible to plasma polymerize materials such as alkanes that do not possess reactive groups. However, this requires that the plasma is provided with sufficient energy to break chemical bonds within the monomers and this results in significant fragmentation and re-arrangement of the precursor molecules as summarized by Heyse et al (Plasma Processes and Polymers, 2007, 4, pg 145-157). As biomolecules, such as collagen, do not possess the reactive groups (e.g. vinyl) expected to take part in a low energy plasma induced polymerization, it is logical to conclude that in order to produce a coating from such a material, high energy plasma parameters would be required in order to induce bond breakage within the molecule. This would induce significant damage to the biomolecule and would be expected to render the molecule biologically inactive. Therefore, development has focused on ways to indirectly attach molecules to a plasma coated surface.

One common method was to first deposit a plasma coating and then attach the biomolecules in a separate step via wet chemical techniques. However, this results in a multi-step process with high costs and there is therefore a requirement for a more rapid, single step approach using plasma technology. Alternatively, plasma systems have been used to deposit coatings onto which biomolecules can be subsequently attached in another multistep process. This area has been thoroughly reviewed by Kim Shyong Siow et al. in Plasma Processes and Polymers, 2006, Volume 3, pages 392-418.

As most biomolecules do not possess vinyl groups or other chemical functionalities that would be expected to undergo free radical style polymerization reactions, it was previously believed that in order to form a plasma coating containing such molecules it was necessary to physically entrap these molecules within a polymer film formed from traditional plasma reactive monomers containing vinyl groups or equivalent chemistry. The biomolecule was therefore mixed with the reactive monomer within the plasma and as the reactive monomer underwent film forming reactions, this allowed the biomolecule to be physically entrapped within the growing coating, as described in WO2005/110626 and WO2005/106477. The downside of this process is that the coating would contain significant amounts of chemical polymers that are not biocompatible and can induce inflammatory responses in a biological setting.

WO 2005/110626 describes the use of a non-thermal plasma device to convert a liquid aerosol containing an active agent and a reactive monomer into a dry coating which contains both a polymer (produced by polymerising the reactive monomer) and an active agent which is physically entrapped in the polymer coating. The patent specifically refers to the coating of medical implants and refers to the incorporation of a biopolymer (collagen) as an active agent. Similarly, WO 2005/106477 describes an atmospheric pressure non-thermal plasma process to deposit biomolecule containing coatings. The process involves the introduction of reactive monomers and biomolecules (proteins, sugars, physiologically active substances, biomimetic materials) into the plasma to produce a polymerised coating of the reactive monomer which entraps the active agent on a surface through the incorporation of the biomolecule into a polymer matrix WO 2010/105829 discloses a technology for the deposition of biomolecules using plasma wherein the biomolecules are introduced as a vapour into the plasma. The patent discloses the concept of spraying a solution into a chamber, evaporating the solvent and then plasma polymerising the evaporated biomolecule to form a coating on a surface. The patent description mentions the use of bioactive molecules (proteins, polysaccharides, etc.) onto various surfaces, including implantable devices.

Argon plasma coagulation (APC) is also a well known technique used in medicine and US 2007/0225700 described typical applications of this technique. The APC systems use an argon plasma to alter tissue through a combination of protein coagulation and tissue dehydration. However, no care is taken to control which proteins are present in the coagulation region and the technique has never been applied to a medical implant.

SUMMARY OF THE INVENTION

One embodiment disclosed herein is directed to overcoming precursor fragmentation induced by traditional plasma devices, and the use of these traditional plasma devices to directly deposit functional coatings from high molecular weight biomolecules.

Another embodiment discloses the use of plasma devices for the deposition of biomolecules or living cells onto a surface of a substrate, such as conductive metal substrates, overcoming previous problems with the treatment of conductive metal substrates due to the formation of high energy arcs.

Another embodiment discloses the use of plasma devices for the deposition of biomolecules or living cells, and/or pre-polymerised biopolymers that do not undergo polymerisation when exposed to traditional polymerisation systems such as free radicals or UV light. As these molecules already have large molecule weights, even a slight degree of coagulation results in a solid coating.

Another embodiment provides a method of depositing only a biomolecule in the absence of a reactive monomer.

Another embodiment describes the use of plasma devices for deposition of biomolecules, overcoming prior art problems such as where the deposition is limited to gas phase systems and requires heating of the precursor solution, which is likely to denature many biomolecules.

Also disclosed herein are surface modification techniques that allow for a single step deposition of biomolecules and/or living cells onto a surface without the use of vacuum systems or additional reactive monomers. By introducing solutions comprising biomolecules into a non-thermal atmospheric pressure plasma, it is possible to create direct binding of the biomolecules to the implant surface. This does not involve polymerisation of the biomolecule, e.g., a biopolymer, but instead involves some cross-linking of the biopolymer strands with additional formation of bonds to the activated substrate surface. In effect, the plasma can be used to initiate coagulation of the biological materials to form a coating.

Additionally, it is possible to achieve the deposition of living cells on an implant surface with or without the presence of additional biomolecules.

DETAILED DESCRIPTION OF THE INVENTION

Figure 1:
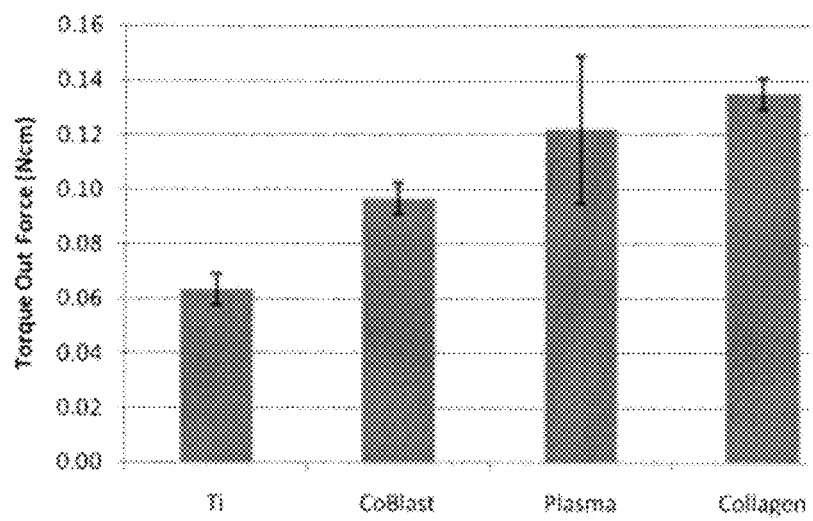
FIG. 1 is a bar graph illustrating the data in Example 1.

The process described herein involves dissolving at least one biomolecule to form a solution; nebulizing the solution, for example with a gas, to form a liquid aerosol; combining the liquid aerosol and a plasma to form a coating; and depositing, in the absence of reactive monomers, the coating onto a substrate surface. This results in the nebulized biomolecules undergoing activation within the plasma and forming a dry coagulated coating on the surface. Unexpectedly, it has been found that this process does not deactivate the biomolecules and a high degree of bioactivity can be retained in the resulting coating.

The at least one biomolecule for use in the disclosed process can be a resorbable biopolymer, a naturally derived biopolymer, a protein, and/or a polysaccharide. In an aspect, the at least one biomolecule is collagen. The resorbable biopolymer can include, but is not limited to chitosan, fibrinogen, hylauronic acid, fibronectin, and phosphorylcholine. Naturally derived biopolymers include, but are not limited to, chitosan, chitin, hyaluronan, starch, polyhydroxyalkanoates, and bacterial cellulose. Proteins, for use herein as a biomolecule, include, but are not limited to, collagen, fibrin, fibrinogen, bone morphogenetic protein (BMP), gelatinn, fibronectin, fibrulin, integrin, and insulin. Polysaccharides include, but are not limited to, α-glycosaminoglycans, alginate, cellulose, chitin, chitosan, hyaluronic acid, and heparin. In an aspect, the at least one biomolecule is a protein involved in blood coagulation.

The coating can also be formed of other biomolecules such as polypeptides, polyglycans, hormones, lipids, interferons, cartilage, therapeutic biologic agents both cellular and synthetically derived, autologous, homologous and allographic and zenographic biologic agents, autologous or homologous, recombinant and synthetic derived blood cells, biomolecules containing antimicrobial/antibiotic agents or bacteriostatic agents, stem cells, stromal cells, fibroblast derived Human Dermal Collagen, matrix proteins, growth factors and cytokines, cells found in loose connective tissue such as endothelial cells, cells found in adipose tissue, macrophages/monocytes, adipocytes, pericytes, reticular cells found in bone marrow stroma, and cultured autologous keratinocytes. The coating may contain mixtures of biomolecules. In an aspect, the biomolecule is a living cell selected from the group consisting of stem cells, progenitor cells, and autologous cells.

The amount of biomolecule present in the coating applied to the substrate can vary depending upon numerous variables including, but not limited to the substrate, and the biomolecule used. In an aspect, the amount of biomolecule present in the coating can be sufficient to completely cover the implant surface and minimize interactions between the implant and the patient's immune system. In orthodpedic applications, the amount of biomolecules can be present in quantities sufficient to promote and enhance bone fixation. In soft tissue applications, the amount of biomolecule present can be sufficient to promote the integration and fixation of the implant into the soft tissue.

The biomolecule can be dissolved in any known solvent, including but not limited to, pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetrnitrile, dimethyl sulfoxide, formic acid, n-butanol, isopropanol, n-propanol, ethanol, methanol, acetic acid, and water. The solvent should not affect the bioactivity of the biomolecule.

Any suitable method can be used to nebulize the solution containing the biomolecule solution. This can include ultrasonic spray systems, rotary nozzles, electrospray devices, hydraulic nozzles, pneumatic spray or gas assisted spray systems. For gas assisted systems, any suitable gas can be used to nebulize the solution comprising the biomolecule. For example, the gas can be selected from the group consisting of nitrogen gas, helium gas, argon gas and mixtures thereof.

The coating can be formed without the addition of any traditional film forming materials. There is no requirement to add precursor materials which undergo standard plasma induced free radical or ionic polymerization through reactive groups such as unsaturated (double or triple bonds), cyclic ring structures, aromatic rings, peroxides, silanes, epoxides or other reactive groups. In an aspect, the method comprises depositing, in the absence of reactive monomers, the aerosol comprising the at least one biomolecule onto a substrate surface. By "reactive monomers" it is understood to include, for example, vinyl groups, cyclic rings or other chemical functionalities that would be expected to undergo free radical style polymerization reactions.

In another aspect, the method for producing a coated substrate can also be performed in the absence of a step of heating of any of the biomolecule, solution, aerosol, etc. The absence of a heating step insures that the biomolecule is not denatured. In a further aspect, the method for producing a coated surface can also be performed in the absence of a vacuum system.

By directly introducing the biomolecule, as an aqueous spray into a low energy atmospheric pressure plasma, it has been found to produce a one step route to the formation of stable, dry, adherent coatings which retain the biological activity of the starting biomolecule.

The substrate for use in the disclosed process can be a medical device, such as an implantable medical device. The medical device can be selected from the group consisting of an orthopaedic, dental, spinal, cranial maxillofacial, and bone trauma fixation implant. In an aspect, the medical device is selected from the group consisting of a stent, an implantable pulse generator, an implantable pump, a valve, an inter-vascular device, a subdermal implant, a transdermal implant, a retinal implant, a cochlear implant, a renal lead or catheter, a trauma lead or catheter, a scaffold lead or catheter, a sensor lead or catheter, and an electrical lead or a catheter.

In the disclosed method, the coating can comprise additional optional ingredients, such as biological active agents and pharmaceutical agents. Exemplary biological active agents include, but are not limited to, vaccines, genetic material, recombinant therapeutic proteins, enzymes, amino acids, steroids, cytokines, growth factors, vitamins, and hormones. Exemplary pharmaceutical agents include, but are not limited to, antibiotics, anti-coagulants, anti-histamines, and anti-inflammatories. In an aspect, the coating can comprise mixtures of at least one biomolecule, at least one biological active agent, and at least one pharmaceutical agent. In a further aspect, the at least one biomolecule is different than the at least one biological active agent.

In another embodiment, there is disclosed of attaching living cells to a substrate surface, comprising introducing a liquid aerosol comprising a solution of living cells into a non-thermal plasma to form plasma-treated living cells; and depositing the plasma-treated living cells onto the substrate surface. As discussed above with regard to the at least one biomolecule, the living cells for use herein, include but are not limited to, stem cells; stromal cells; fibroblast derived Human Dermal Collagen; matrix proteins; growth factors and cytokines; cells found in loose connective tissue such as endothelial cells; cells found in adipose tissue; macrophages/monocytes; adipocytes; pericytes; reticular cells found in bone marrow stroma; cultured autologous keratinocytes; and mixtures thereof.

In an aspect, the solution of living cells can also comprise a biomolecule, such as a resorbable biopolymer, a naturally derived biopolymer, a protein, a polysaccharide, a biological active agent, a pharmaceutical active agent, and mixtures thereof.

The living cells, e.g., autologous material, may be used to improve the biocompatibility of the substrate and/or to reduce implant rejection when the substrate is an implantable medical device. The autologous material may be blood, platelet rich plasma, extracellular fluid, or other living cells, as disclosed above. The autologous material may be taken from the patient and cultured via standard cell culture techniques to form sufficient volumes for use in the disclosed methods.

Embodiments of the present invention employ non-thermal plasma devices where the plasma operates close to room temperature thus allowing the processing of temperature sensitive materials, without imposing a damaging thermal burden onto the material. The temperature of the overall plasma is preferably below about 40 degrees Celsius. Plasma temperatures of up to about 90° C. may be acceptable for short exposure times of less than about 60 seconds. Even in low energy plasma systems, the hot electrons of the plasma create, through high-energy collisions, a rich source of radicals and excited species with a high chemical potential energy capable of chemical and physical reactivity. Non-thermal equilibrium plasmas can be created at ambient pressure and have been reviewed extensively by Roth (Roth J. R., Industrial Plasma Engineering, Volume 2 Applications to Non-thermal Plasma Processing, Institute of Physics Publishing, 2001, pages 37-73). Such plasmas include dielectric barrier discharges, the disclosure of which is hereby incorporated by reference. Another non-thermal equilibrium plasma is the atmospheric pressure glow discharge (APGD) as described by Okazaki et al (J. Phys. D: Appl. Phys., 26, 889-892 (1993)), the disclosure of which is hereby incorporated by reference. These APGD plasmas have been described extensively by Roth as One Atmosphere Uniform Glow Discharge Plasmas (OUAGDP) and are found to operate from 0.5 to 40 kHz. Corona plasma devices can also operate in non-thermal equilibrium mode. Various plasma jets are also capable of operating in a "cold" or non-thermal equilibrium mode. In an aspect, the plasma is a low energy, non-thermal equilibrium atmospheric pressure. In a further aspect, the plasma is pulsed.

For optimum control, the plasma is operated below 500 kHz and preferably below 60 kHz and may be pulsed on and off in a controlled fashion to minimise the energy delivered to the aerosol and substrate. This enables controlled plasma reactions that preserve precursor functionality and do not damage or fragment sensitive active species.

Alternatively, the plasma can be contained between two electrodes, with a grounded electrode separating the object to be treated from the plasma, such that no significant voltage is applied to any object son placed downstream of the device. This can be accomplished using a plasma device such as described by Ladwig et al (Surface & Coatings Technology 201 (2007) 6460-6464), the disclosure of which is hereby incorporated by reference, and would be suitable for the treatment of electrically conductive substrates which may otherwise be subject to electrical arcing.

The plasma parameters (electrode design, frequency, voltage, gas composition, etc.) can be chosen to control the plasma process and ensure that the plasma operates in a non-thermal manner to produce a low-temperature plasma, which does not adversely affect temperature sensitive materials which are being deposited.

In a further embodiment, there is disclosed a method producing a coated substrate, comprising dissolving at least one biomolecule to form a solution; nebulizing the solution with a gas to form a liquid aerosol; introducing the liquid aerosol downstream of a plasma afterglow to form a coating; and depositing, in the absence of reactive monomers, the coating onto a substrate surface. By introducing the liquid aerosol comprising the at least one biomolecule downstream of a plasma chamber outlet, i.e., into the plasma afterglow, damage to the biomolecules is minimized. This allows coatings comprising biomolecules sensitive to temperature, ions, free radicals and other active species present in the liquid aerosol to be deposited where they would otherwise be damaged if the liquid aerosol was introduced directly into the plasma chamber.

The following examples further illustrate aspects of the present disclosure but do not limit the present disclosure

EXAMPLES

Example 1

Deposition of Collagen onto an Orthopaedic Implant

Collagen (bovine derived) was dissolved in purified water to produce a solution having a concentration of 1 mg/ml. The collagen-containing solution was then transferred to a syringe and pumped into a pneumatic nebulizer device (T2100 produced by Burgener Research) at a flow rate of 50 µl/min. The nebulizer created an aerosol spray using helium as the spray gas.

The resulting aerosol was introduced into a non-thermal plasma discharge. The plasma device comprised a metallic pin electrode housed within a plastic dielectric container. Inert gas (helium) was allowed to flow through the container at a flow rate of 5 liters/min and radio frequency (RF) power was supplied to the electrode to produce a plasma discharge. The RF power was supplied at a frequency of ~18 kHz and 15 kV (peak to peak). This device has been described in detail elsewhere (O'Neill & O'Sullivan, Chem Vap Deposition, 2008, 15, pg 1-6), the disclosure of which is hereby incorporated by reference.

The implantable device was a titanium screw which was initially treated with a process called CoBlast (outlined in WO 2008/033897, the disclosure of which is hereby incorporated by reference) to ensure delivery of a roughened hydroxyapatite (HA) surface finish. The HA-treated screw was then placed beside the outlet of the plasma device and rotated at a speed of circa 60 Hertz to ensure a uniform exposure to the plasma and aerosol.

The treated screws were then implanted into the femur of various rabbits using a modified version of the procedure outlined by Hunt et al. (*Biomaterials, Volume* 26, *Issue* 29, October 2005, Pages 5890-5897), the disclosure of which is hereby incorporated by reference. Pilot holes were created in each femur and the screws were inserted at a constant torque using a force gauge. For comparison, the following controls were used:

(1) Untreated titanium screw with anodised surface finish.

(2) A hydroxyapatite coating produced by the process outlined in WO2008/033897, hereafter referred to as "CoBlast HA".

(3) An industry standard HA coating produced by thermal plasma spraying, hereafter referred to as "Plasma HA".

After 14 days the animals were sacrificed and the screws were extracted. The force required to remove each screw was recorded and the results are plotted below. As is evident from the graph, the two HA coatings (Plasma and CoBlast) significantly outperformed the untreated Ti screw as both HA surfaces exhibit significant increases in the torque force required to remove the screws. Although the mean force required to extract the Plasma HA sample was slightly higher than that of the CoBlast samples, the Plasma HA sample also exhibited a high degree of variability which is not a desired outcome. See the data in FIG. 1, which illustrates the extraction torque at day 14 for various treated substrates.

While the HA surface treatments both improved the early stage fixation of the titanium implant, the highest overall torque out values were produced by the collagen coating which was applied over the CoBlast surface. This indicates that the collagen treatment produced significantly enhanced bone fixation. The torque out force was also highly reproducible on these samples, confirming that the surface is highly stable and reproducible. When compared to the other three standard control surfaces, it is evident that the plasma deposited collagen clearly outperforms all of the other samples.

Example 2

Deposition of Collagen and Fibronectin onto PEEK and In Vitro Evaluation of Biocompatibility Polyether ether ketone (PEEK) discs (diameter 10 mm, thickness approximately 5 mm) were cleaned in ultrasonic water, rinsed with isopropyl alcohol (IPA) and air dried. The samples were then divided into 3 groups: (1) Collagen coating, (2) Fibronectin coating, (3) Unmodified PEEK. Samples to be coated with collagen were treated as follows: As in Example 1, the collagen was diluted to a concentration of 1 mg/ml and atomized at a rate of 25 microliters/minute using a Burgener T2100 nebuliser. The resultant aerosol was sprayed directly into a plasma contained within a Teflon chamber (diameter of 16 mm and a length of 45 mm). The plasma was created by passing approximately 3 liters/minute of helium past a metal pin electrode connected to a PTI power supply producing circa 15 kV (peak-peak) at a frequency of 18 kHz operating at an input power of 60 W. Samples were exposed to the mixture of plasma and aerosol exiting the chamber by placing the substrate adjacent to the plasma exit and each sample was coated for 1 minute.

Fibronectin samples were produced in a similar manner, but the fibronectin solution contained significant levels of NaCl and this conductive solution produced some arcing in the liquid delivery line. As a consequence, the plasma power and deposition time were reduced when compared to the collagen coating. The plasma power was reduced to 50 W, the flowrate was increased to 35 microliters/minute and the deposition time was reduced to 30 seconds per sample.

SEM analysis showed no evidence of alterations in the surface topography of either the collagen or fibronectin samples after treatment, suggesting a conformal coating had been deposited. However XPS analysis of the surfaces showed increases in nitrogen levels consistent with the deposition of either collagen or fibronectin respectively on the coated PEEK surfaces, as shown in Table 1. Traces of chlorine were also detected on the fibronectin samples consistent with the presence of salts in the starting solution.

TABLE 1

XPS analysis of PEEK samples

| | PEEK | PEEK + Col | PEEK + Fib |
|---|---|---|---|
| C | 87.7 | 74.5 | 65.9 |
| O | 12.3 | 17.7 | 12.8 |
| N | 0 | 7.8 | 20.0 |
| Cl | 0 | | 1.4 |

Figure 2:
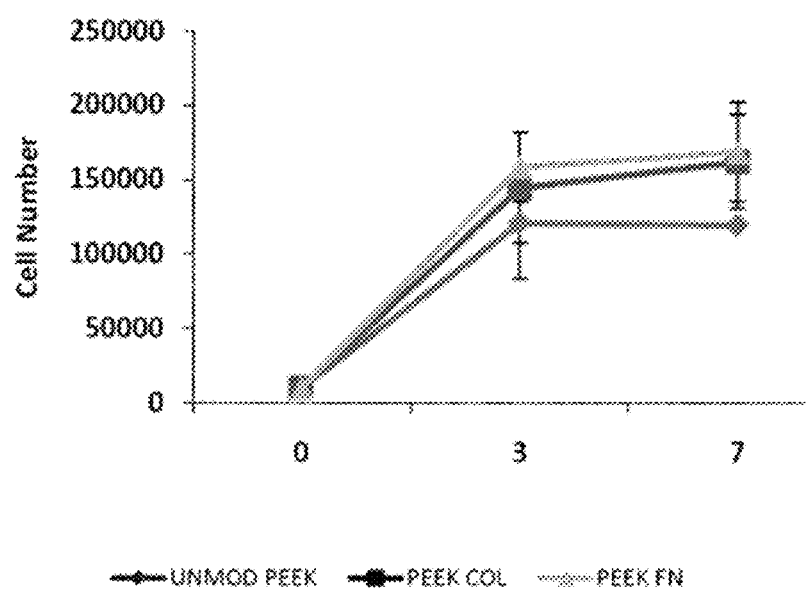
FIG. 2 is a line graph illustrating the data in Example 2.

Samples were then submitted to an independent academic laboratory for in vitro cell culture studies. Surfaces were seeded with human mesenchymal stem cells, and cell viability and proliferation were examined over a seven day period. Treatment of the PEEK surfaces with collagen or fibronectin appeared to increase the viability of cells on the surface. This was attributed to increased cell proliferation on these surfaces when compared to the unmodified PEEK, as shown in FIG. 2, cell proliferation data for in vitro samples at days 0, 3 & 7.

The combination of elemental composition from XPS and enhanced cell proliferation from the in vitro studies confirms that the plasma technique described herein is capable of depositing high weight biomolecules onto a surface as a coating and also retains the biological activity of the biomolecules.

Example 3

Deposition of Autologous Material

A plasma device was created by connecting a Redline G2000 power supply to a metal pin inserted into a 10 mm diameter×60 mm long plastic tube which was sealed at one end except for a gas entry port and the metal pin. Whole blood was drawn from a healthy volunteer and stored in a blood collection tube coated with heparin to prevent coagulation. The blood was then sprayed through a T2100 nebulizer (Burgener Research) at a rate of 25 microliters per minute and the resultant aerosol was directed through the gas entry port into the plastic tube along with a flow of 5 liters/minute of helium. Glass substrates were placed 5 mm from the exit of the tube to collect the sprayed blood sample. When no power was applied (no plasma), the blood was found to collect on the substrate as a wet sprayed pool. However, when plasma was formed within the tube by applying power (100 kHz, 45% duty cycle) from the G2000 power supply unit, this was found to directly alter the state of the aerosolized blood. At low levels of applied power (7.2 kV peak to peak), the coating was found to have a moist, gel-like consistency. At higher power levels (8.4 kV), the coating was a dry adherent coating. Optical microscopy at 40× magnification confirmed that the coating contained numerous viable blood cells. At powers greater than 10 kV, the coating was found to be highly cured and appeared to be heavily altered by the plasma. There were significantly reduced numbers of viable cells. This confirms that low power (>7.5 kV using these equipment settings) plasma treatment was effective at producing a coating, but that higher powers (>8 kV in this example) can damage the biomolecules or living cells.

At numerous places throughout this specification, reference has been made to a number of U.S. patents, published foreign patent applications and published technical papers. All such cited documents are expressly incorporated in full into this disclosure as if fully set forth herein.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a biomolecule" includes two or more different biomolecules. As used herein, the term "include" and its grammatical variants are intended to be non-limiting, such that recitation of items in a list is not to the exclusion of other like items that can be substituted or added to the listed items.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

Applicant does not intend to dedicate any disclosed embodiments to the public, and to the extent any disclosed modifications or alterations may not literally fall within the scope of the claims, they are considered to be part of the invention under the doctrine of equivalents.

The invention claimed is:

1. A method of producing a coated substrate, comprising: dissolving at least one biomolecule in a solvent to form a solution;
nebulizing the solution to form a liquid aerosol;
introducing the liquid aerosol into a plasma; and then
exposing a substrate to the liquid aerosol and the plasma to deposit, in the absence of reactive monomers, a coating comprising the at least one biomolecule onto the substrate.

2. The method of claim 1, wherein the plasma is a non-thermal atmospheric pressure discharge.

3. The method of claim 1, wherein the coating comprises a coagulated biomolecule.

4. The method of claim 1, wherein the coating comprises a material that is enzymatically biodegraded in the human body.

5. The method of claim 1, wherein the at least one biomolecule comprises collagen.

6. The method of claim 1, wherein the at least one biomolecule comprises a resorbable biopolymer selected from the group consisting of chitosan, fibrinogen, hylauronic acid, fibronectin, and phosphorylcholine.

7. The method of claim 1, wherein the at least one biomolecule comprises a naturally derived biopolymer selected from the group consisting of chitosan, chitin, hyaluronan, starch, polyhydroxyalkanoates, and bacterial cellulose.

8. The method of claim 1, wherein the at least one biomolecule comprises a protein selected from the group consisting of collagen, fibrin, fibrinogen, bone morphogenetic protein (BMP), gelatin, fibronectin, fibrulin, integrin, and insulin.

9. The method of claim 1, wherein the at least one biomolecule comprises a polysaccharide selected from the group consisting of a-glycosaminoglycans, alginate, cellulose, chitin, chitosan, hyaluronic acid, and heparin.

10. The method of claim 1, wherein the at least one biomolecule comprises a protein involved in blood coagulation.

11. The method of claim 1, wherein the substrate is a medical device and is selected from the group consisting of an orthopaedic implant, a dental implant, a spinal implant, a cranial maxillofacial implant, and a bone trauma fixation implant.

12. The method of claim 1, wherein the substrate is a medical device selected from the group consisting of a stent, an implantable pulse generator, an implantable pump, a valve, an inter-vascular device, a subdermal implant, a transdermal implant, a retinal implant, a cochlear implant, a renal lead, a renal catheter, a trauma lead, a trauma catheter, a scaffold lead, a scaffold catheter, a sensor lead, a sensor catheter, an electrical lead, and a catheter.

13. The method of claim 1, wherein the coating further comprises at least one biological active agent selected from the group consisting of vaccines, genetic material, recombinant therapeutic proteins, enzymes, amino acids, steroids, cytokines, growth factors, vitamins, and hormones.

14. The method of claim 13, wherein the at least one biological active agent may be the same or different than the at least one biomolecule.

15. The method of claim 1, wherein the coating further comprises at least one pharmaceutical agent selected from the group consisting of antibiotics, anti-coagulants, anti-histamines, and anti-inflammatories.

16. The method of claim 1, wherein the plasma is pulsed.

17. A method of attaching living cells to a substrate surface, comprising:
    introducing a liquid aerosol comprising a solution of living cells into a non-thermal plasma to form plasma-treated living cells; and
    depositing the plasma-treated living cells onto the substrate surface.

18. The method of claim 17, wherein the solution of living cells further comprises at least one biopolymer.

19. The method of claim 17, wherein the solution of living cells is derived from a patient or from the patient's blood.

20. A method of producing a coated substrate, comprising:
    dissolving at least one biomolecule in a solvent to form a solution;
    nebulizing the solution to form a liquid aerosol;
    introducing the liquid aerosol into a plasma afterglow; and then
    exposing a substrate to the liquid aerosol and the plasma afterglow to deposit, in the absence of reactive monomers, a coating comprising the at least one biomolecule onto the substrate.

21. A method of producing a coated substrate, comprising:
    dissolving at least one biomolecule in a solvent to form a solution, the at least one biomolecule having biological activity;
    nebulizing the solution to form a liquid aerosol;
    introducing the liquid aerosol into a plasma; and then
    exposing a substrate to the liquid aerosol and the plasma to deposit, in the absence of reactive monomers, a coating onto the substrate;
    wherein the coating retains biological activity of the at least one biomolecule.

22. A method of producing a coated substrate, comprising:
    dissolving at least one biomolecule in a solvent to form a solution;
    nebulizing the solution to form a liquid aerosol;
    introducing the liquid aerosol into a plasma; and then
    exposing a substrate to the liquid aerosol and the plasma to deposit, in the absence of reactive monomers, a coating comprising the at least one biomolecule onto the substrate, wherein the substrate is exposed to the liquid aerosol and the plasma at atmospheric pressure.

\* \* \* \* \*